US009603359B2

(12) United States Patent
Joshi (10) Patent No.: US 9,603,359 B2
(45) Date of Patent: Mar. 28, 2017

(54) ANTI-MICROBIAL DISINFECTANT WIPE AND METHOD OF USE

(71) Applicant: Microlin, LLC, Salt Lake City, UT (US)

(72) Inventor: Ashok V. Joshi, Salt Lake City, UT (US)

(73) Assignee: Microlin, LLC, Salt Lake City, UT (US)

(*) Notice: Subject to any disclaimer, the term of this patent is extended or adjusted under 35 U.S.C. 154(b) by 25 days.

(21) Appl. No.: 14/314,862

(22) Filed: Jun. 25, 2014

(65) Prior Publication Data

US 2015/0001066 A1 Jan. 1, 2015

Related U.S. Application Data (60) Provisional application No. 61/839,986, filed on Jun. 27, 2013, provisional application No. 61/846,164, filed on Jul. 15, 2013.

(51) Int. Cl.

| C25B 9/00 | (2006.01) |
|---|---|
| C25B 9/06 | (2006.01) |
| A01N 59/02 | (2006.01) |
| A01N 33/12 | (2006.01) |
| A01N 25/34 | (2006.01) |
| A01N 43/66 | (2006.01) |
| A01N 59/00 | (2006.01) |
| A01N 59/16 | (2006.01) |

(Continued)

(52) U.S. Cl.
CPC .............. *A01N 25/34* (2013.01); *A01N 33/12* (2013.01); *A01N 43/66* (2013.01); *A01N 59/00* (2013.01); *A01N 59/02* (2013.01); *A01N 59/16* (2013.01); *A61L 2/18* (2013.01); *C25B 1/26* (2013.01); *C25B 9/06* (2013.01); *A61L 2202/11* (2013.01)

(58) Field of Classification Search
CPC .... C25B 9/00; C25B 9/06; C25B 1/26; A01N 43/66; A01N 59/02; A01N 59/00; A01N 33/12; A01N 59/16
USPC .................................................. 204/242, 248
See application file for complete search history.

(56) References Cited

U.S. PATENT DOCUMENTS

| 6,916,480 B2 | 7/2005 | Anderson et al. |
| 7,446,082 B2 * | 11/2008 | Kilkenny ............... A01N 37/36 |
| | | 510/191 |

(Continued)

FOREIGN PATENT DOCUMENTS

| EP | 2168604 A1 | 3/2010 |
| JP | 2006-189883 A | 7/1994 |
| WO | 03-070004 A1 | 8/2003 |

OTHER PUBLICATIONS

NHO "Written Opinion of the International Searching Authority" Application No. PCT/US2014/044111, 9 pages, mailed Oct. 21, 2014.

*Primary Examiner* — Zulmariam Mendez
(74) *Attorney, Agent, or Firm* — Brian C. Trask (57) ABSTRACT

A wipe for anti-microbial disinfecting includes a flexible substrate and an anti-microbial ion source integrated on the substrate. The flexible substrate is made entirely or in part of woven fiber cloth, non-woven fiber cloth, woven synthetic cloth, non-woven synthetic cloth, or natural fiber cloth. The anti-microbial ion source is configured to dissolve in an aqueous solution to form an anti-microbial solution. The flexible substrate is configured to absorb the anti-microbial solution for use in cleaning.

15 Claims, 6 Drawing Sheets

(51) Int. Cl.
 *C25B 1/26* (2006.01)
 *A61L 2/18* (2006.01)

(56) References Cited

U.S. PATENT DOCUMENTS

2005/0079987 A1  4/2005  Cartwright et al.
2011/0118655 A1  5/2011  Fassih et al.

* cited by examiner

ANTI-MICROBIAL DISINFECTANT WIPE AND METHOD OF USE

CROSS-REFERENCE TO RELATED APPLICATIONS

This application claims the benefit of U.S. Provisional Application No. 61/839,986, filed on Jun. 27, 2013, and U.S. Provisional Application No. 61/846,164, filed on Jul. 15, 2013, each of which is incorporated by reference herein in its entirety.

TECHNICAL FIELD

The present disclosure relates to anti-microbial wipes. In particular, the present disclosure relates to anti-microbial wipes configured to be activated upon exposure to an aqueous solution.

BACKGROUND

Many objects and surfaces used in a variety of applications call for clean surfaces and decontamination processes. Decontaminated surfaces are used hospital and other medical environments, industrial fabrication environments, laboratory environments, work spaces, personal spaces, and other similar environments. Anti-microbial disinfectants kill bacteria on objects and surfaces and wipes with anti-microbial disinfectants allow for simple and efficient decontamination.

SUMMARY

Embodiments of a wipe for anti-microbial disinfecting are described. In one embodiment, the wipe for anti-microbial disinfecting includes a flexible substrate and an anti-microbial ion source integrated on the substrate. The flexible substrate is made entirely or in part of woven fiber cloth, non-woven fiber cloth, woven synthetic cloth, non-woven synthetic cloth, or natural fiber cloth. The anti-microbial ion source is configured to dissolve in an aqueous solution to form an anti-microbial solution. The flexible substrate is configured to absorb the anti-microbial solution for use in cleaning. Other embodiments of a wipe for anti-microbial disinfecting are also described.

In one embodiment, the wipe for anti-microbial disinfecting includes a flexible substrate, and an anode and a cathode attached to the flexible substrate. The flexible substrate is made entirely or in part of woven fiber cloth, non-woven fiber cloth, woven synthetic cloth, non-woven synthetic cloth, or natural fiber cloth. At least one of the anode, the cathode, and flexible substrate comprises an anti-microbial ion source, and the wipe is configured to form a galvanic cell when an aqueous solution contacts the anode and the cathode. The galvanic cell is configured to cause the anti-microbial ion source to create an anti-microbial solution. Other embodiments of a wipe for anti-microbial disinfecting are also described.

In one embodiment, the wipe for anti-microbial disinfecting includes a flexible substrate, an anode and a cathode attached to the flexible substrate, and a power source in operable communication with the anode and the cathode. The flexible substrate is made entirely or in part of woven fiber cloth, non-woven fiber cloth, woven synthetic cloth, non-woven synthetic cloth, or natural fiber cloth. At least one of the anode, the cathode, and flexible substrate comprises an anti-microbial ion source. The anode, cathode, and anti-microbial ion source is configured to form an electrolytic cell when an aqueous solution contacts the anode and the cathode, and a reaction of the electrolytic cell is configured to create an anti-microbial solution. Other embodiments of a wipe for anti-microbial disinfecting are also described. Embodiments of methods for using the wipes are also described.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

Throughout the description, similar reference numbers may be used to identify similar elements.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments relate to anti-microbial disinfecting wipes. Some embodiments involve anti-microbial material connected to or embedded in a flexible substrate or cloth that when exposed to an aqueous solution dissolves into an anti-microbial solution that is absorbed by the cloth and then used to clean. Some embodiments utilize a galvanic cell or an electrolytic cell connected to or embedded in a flexible substrate or cloth, where when exposed to an aqueous solution converts an anti-microbial ion source into an anti-microbial solution that is absorbed by the cloth and then used to clean. Some embodiments involve a flexible substrate or cloth with at least a portion of a galvanic cell connected to or embedded in the flexible substrate or cloth, and where the anode, cathode, or substrate includes an anti-bacterial ion source, which when the anode and cathode are exposed to an aqueous solution, the anti-bacterial ion source is converted to an anti-microbial solution that is absorbed by the cloth and then used to clean. Some embodiments involve a flexible substrate or cloth with at least a portion of a electrolytic cell connected to or embedded in the flexible substrate or cloth, and where the anode, cathode, or substrate includes an anti-bacterial ion source, which when the anode and cathode are exposed to an aqueous solution and a power source, the anti-bacterial ion source is converted to an anti-microbial solution that is absorbed by the cloth and then used to clean.

Some embodiments allow for anti-microbial disinfecting wipes to be stored in a de-active state and ready to be activated right before use of the wipes. Some embodiments allows for activation of the wipes upon contact with an aqueous solution. Activation of the wipes converts an anti-microbial ion source (or anti-microbial material) into an anti-microbial solution that is absorbed by the wipe and used for wiping and cleaning objects and surfaces. Some embodiments allow for the tracking and notifying of when the anti-microbial solution is at an optimal level to ensure better disinfecting results.

Anti-microbial solutions that incorporate silver ions are effective disinfectants with several advantages over other disinfecting solutions. Anti-microbial solutions effectively disinfect against a variety of microbes including bacteria, antibiotic resistant bacteria, viruses, and fungi. Silver ion anti-microbial solutions have a very low toxicity towards humans, pets, livestock, and the environment. Silver ion anti-microbial solutions are generally non-flammable, non-corrosive, odorless, fumeless, and non-skin irritating. Silver ion anti-microbial solutions generally require no additional alcohol, bleach, or other toxic ingredients.

The Figures described below depict some embodiments of anti-microbial disinfectant wipes and electrochemically-activated anti-microbial disinfectant wipes, but should be construed as non-limiting representations of the wipe and non-limiting representations of the locations of the individually described elements with respect to each other and with respect to the entire wipe. The elements have been depicted relative to each other and relative to the entire wipe only for illustrative purposes and only for ease of explanation. A person skilled in the art will understand that the wipe and associated methods of using the wipe can be implemented and used without employing these specific details.

Figure 1:
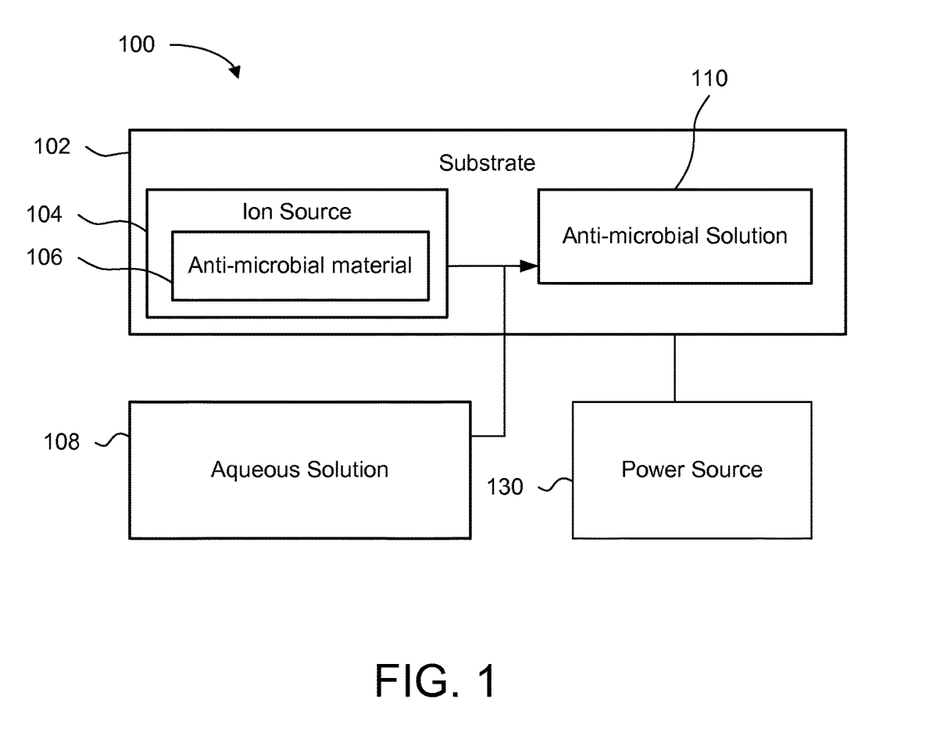
FIG. 1 depicts a schematic diagram of one embodiment of an anti-microbial disinfecting wipe.

FIG. 1 depicts a schematic diagram of one embodiment of an anti-microbial disinfecting wipe 100. Although the illustrated wipe 100 is shown and described with certain components and functionality and in conjunction with certain components, other embodiments of the wipe 100 may include fewer or more components to implement less or more functionality.

In the illustrated embodiment, the wipe 100 comprises a substrate 102 and an anti-microbial ion source 104. In some embodiments, when the anti-microbial ion source 104 is contacted by an aqueous solution 108, the anti-microbial ion source 104 dissolves into an anti-microbial ion solution 110. The substrate 102 may be flexible or firm. In some embodiments the substrate 102 comprises a woven, fiber cloth. In some embodiments the substrate 102 comprises a non-woven, fiber cloth. In some embodiments the substrate 102 comprises a woven, synthetic cloth. In some embodiments the substrate 102 comprises a non-woven, synthetic cloth. In some embodiments the substrate 102 comprises a natural fiber cloth. In some embodiments the substrate 102 is configured for a single use. In some embodiments the substrate 102 is configured for a multiple uses. In some embodiments the substrate 102 is configured in size to be used with a single hand.

The illustrated substrate 102 comprises woven, fiber cloth. The substrate 102 is moistened with an aqueous solution 108 (e.g., water or other appropriate solution). The water or other appropriate solution activates the anti-microbial ion source 104 to create anti-microbial ions in an anti-microbial ion solution 110 that is absorbed into the substrate 102. The substrate 102 and the absorbed anti-microbial ion solution 110 are then used for disinfecting surfaces. It will be readily understood by those having skill in the art that term anti-microbial includes anti-bacterial and anti-fungal.

In some embodiments, a method of use of the wipe 100 comprises moistening the substrate 102 with an aqueous solution 108, activating the anti-microbial ion source 104 to create an anti-microbial solution 110, and disinfecting surfaces with the substrate 102 and the absorbed anti-microbial solution 110.

In the illustrated embodiment, the ion source 104 comprises an anti-microbial material. Non-limiting examples of anti-microbial materials, disinfectant, and/or cleansing agents that may be used herein include potassium peroxymonosulfate, calcium carbonate, and quaternary ammonium compounds, such as benzalkonium chloride, dodecyl dimethyl benzyl ammonium chloride, and lauryl dimethyl benzyl ammonium chloride. In some embodiments, the ion source 104 may be a silver ion source and may be replaced by a sufficient amount of the desired active agent and be used in substantially the same way disclosed above.

In some embodiments, the anti-microbial material 104 is a silver ion source selected from silver dihydrogen citrate, silver nitrate, silver fluoride, silver acetate, silver permanganate, silver sulfate, silver nitrite, silver bromate, silver salicylate, silver iodate, silver dichromate, silver chromate, silver carbonate, silver citrate, silver phosphate, silver chloride, or mixtures thereof.

In some embodiments, the anti-microbial material 104 is at least one of the following: sodium dichloroisocyanurate, potassium peroxymonosulfate, calcium hypochlorite, benzalkonium chloride, dodecyl dimethyl benzyl ammonium chloride, lauryl dimethyl benzyl ammonium chloride, quaternary ammonium salt, and sodium per carbonate.

In some embodiments, the ion source 104 is configured such that an optimal concentration of silver ions is approximated in the silver ion anti-microbial solution. In some embodiments, the optimal concentration of silver ions is about 0.03 g/L. In some embodiments, the optimal concentration of silver ions is between about 0.02 and 0.04 g/L. In some embodiments, the optimal concentration of silver ions is between about 0.001 and 0.05 g/L. In some embodiments the ion source 102 comprises a mixture of a silver compound and an ionic compound including a counterion in common with the silver compound. In some embodiments, the ion source 104 comprises a mixture of a silver compound and an ionic compound with a counterion in common with the silver compound formulated such that the optimal concentration of silver ion is maintained by the common ion effect. In some embodiments, the ion source 104 comprises a mixture of more soluble silver compounds and less soluble silver compounds. In some embodiments, the ion source 104 comprises a mixture of more soluble silver compounds and less soluble silver compounds formulated such that the optimal concentration of silver ions is maintained in the silver ion anti-microbial solution.

In some embodiments, the ion source 104 comprises a solid form, a granular form, a powder form, a pellet form, and/or a matrix form. In some embodiments, the matrix form is configured to allow for slow release of the ions. In some embodiments, the ion source 104 is configured to be embedded into the flexible substrate 102. In some embodiments, the ion source 104 is configured to be printed onto the flexible substrate 102 in the form of an ink. In some embodiments, for manufacturing convenience, a silver ion source ink can be screen printed onto the flexible substrate 102 to make the anti-microbial disinfectant wipe 100. In some embodiments, for manufacturing convenience, the silver ion source ink can be ink jet printed onto the flexible substrate 102. In some embodiments, the anti-microbial material 106 comprises nano-particles. The nano-particles may be instantaneously dissolvable. In some embodiments, the anti-microbial material 106 may be a combination of different sizes to allow for dissolution at different rates. For example, a portion of the anti-microbial material 106 may be nano-particles configured to be instantaneously dissolvable in the aqueous solution 108, while another portion of the anti-microbial material 106 may be of another form dissolvable at a slower rate.

The skilled artisan will understand that more soluble silver compounds and/or less soluble silver compounds and/or other compounds can be combined to formulate a silver ion source 104 that achieves an optimal silver ion concentration upon dissolution. Silver compounds may be combined in some embodiments to formulate a silver ion source 104 that achieves an optimal silver ion concentration. A person skilled in the art will understand that silver compounds that are more soluble can be combined with silver compounds that are less soluble to formulate a silver ion source 104 that achieves an optimal silver ion concentration.

As an example, a silver ion source 104 includes a single silver compound 106 in the form of an ink that is printed onto a flexible substrate 102 and allowed to dry. The solid matrix contains a soluble silver source 104 that can be dissolved to form silver ions and create sufficient silver ion anti-microbial solution 110 for a single wipe 100. In the example, the single silver compound 106 is silver carbonate with a solubility of 0.033 g/L for the compound with 78.23% of the compound comprising silver ions. Therefore a saturated solution of silver carbonate possesses a concentration of about 0.026 g/L of silver ions. This concentration of 0.026 g/L of silver ions is within the optimal silver ion concentration of about 0.02 to 0.04 g/L disclosed herein and therefore a saturated solution of silver carbonate is effective as an anti-microbial material for creation of a silver ion anti-microbial solution 110. The silver ion source ink is formulated such that when printed, a single wipe 100 contains at least about 0.000066 g of silver carbonate. The printed wipe is then moistened with 2 ml of distilled water (aqueous solution 108) and the silver ion source ink is allowed to dissolve and to create the silver ion anti-microbial solution 110. Lastly, the wipe 100 is used to disinfect surfaces.

As another example, the protocol of the previous example is followed with the exception that highly soluble silver nitrate comprises the single silver compound (anti-microbial material 106). Silver nitrate has a solubility of 2570 g/L for the compound with 63.5% of the compound comprising silver ions. To achieve an optimal silver ion concentration of about 0.03 g/L of silver ions in 2 ml of water, 0.00006 g of silver ions need to be available for dissolution. To provide the required 0.00006 g of available silver ions, 0.0000945 g of silver nitrate is printed onto the flexible substrate 102. All other steps of the protocol are carried out as in the previous example.

As another example, the protocol of previous two examples is followed with the exception that silver salicylate comprises the single silver compound (anti-microbial material 106). Silver salicylate has a solubility of 0.95 g/L for the compound with 44.02% of the compound comprising silver ions. To achieve an optimal silver ion concentration of about 0.03 g/L of silver ions in 2 ml of water, 0.00006 g of silver ions need to be available for dissolution. To provide the required 0.00006 g of available silver ions, 0.000136 g of silver salicylate is printed onto the flexible substrate 102. All other steps of the protocol are carried out as in the previous two examples.

While the foregoing discloses anti-microbial, disinfectant, and/or cleansing solutions that incorporate silver ions that are prepared in situ and on demand from a silver ion source 104, the disclosed embodiments may be advantageously used in relation to non-silver-based anti-microbial materials (as disclosed above), disinfectants, and/or cleansing solutions that may be prepared by dissolving a solid active ingredient in an aqueous solution 108 according to the principles disclosed above.

In some embodiments, the active ingredient of the non-silver-based anti-microbial material 106 is configured to be printed on the flexible substrate 102 in the form of an ink.

For manufacturing convenience, the solid, active ingredient of the non-silver-based anti-microbial material 106 is screen printed onto the flexible substrate 102 to make the anti-microbial disinfectant wipe 100.

In some embodiments, the appropriate aqueous solution 108 to moisten the substrate 102 may be tap water, purified water, de-ionized water, and/or distilled water. In some embodiments, the appropriate aqueous solution 108 to moisten the substrate 102 is an acidic solution. In some embodiments, the appropriate aqueous solution 108 to moisten the substrate 102 is a solution of a weak acid. In some embodiments, the appropriate aqueous solution 108 to moisten the substrate 102 is an organic acid solution. In some embodiments, the appropriate aqueous solution 108 to moisten the substrate 102 is a citric acid solution. In some embodiments, the appropriate aqueous solution 108 to moisten the substrate 102 is a citric acid solution prepared with juice from citrus fruit. In other embodiments, the appropriate aqueous solution 108 to moisten the substrate 102 is an ionic solution. In other embodiments, the appropriate aqueous solution 108 to moisten the substrate 102 is a sodium chloride solution. In other embodiments, the appropriate aqueous solution 108 to moisten the substrate 102 is a salt solution. A person having skill in the art will readily recognize that the term aqueous solution 108 includes the preceding solution embodiments.

Some embodiments include a power source 130, where the power source 130 provides an alternating current to electrodes imprinted or embedded in the substrate 102. An alternating electric field is created to further disinfect the surface and inhibit microbial growth in addition to the disinfecting functionality of the anti-microbial solution 110. As is discussed more fully below electrodes may be printed or embedded into a flexible substrate 102. An external power source 130 can be used to create the alternating electric field. The external power source 130 may be part of a handle or other apparatus discussed more fully below. The external power source 130 in such embodiments may be anything that generates an alternating current. In one example, a battery and a DC to AC power inverter may be used.

Figure 2:
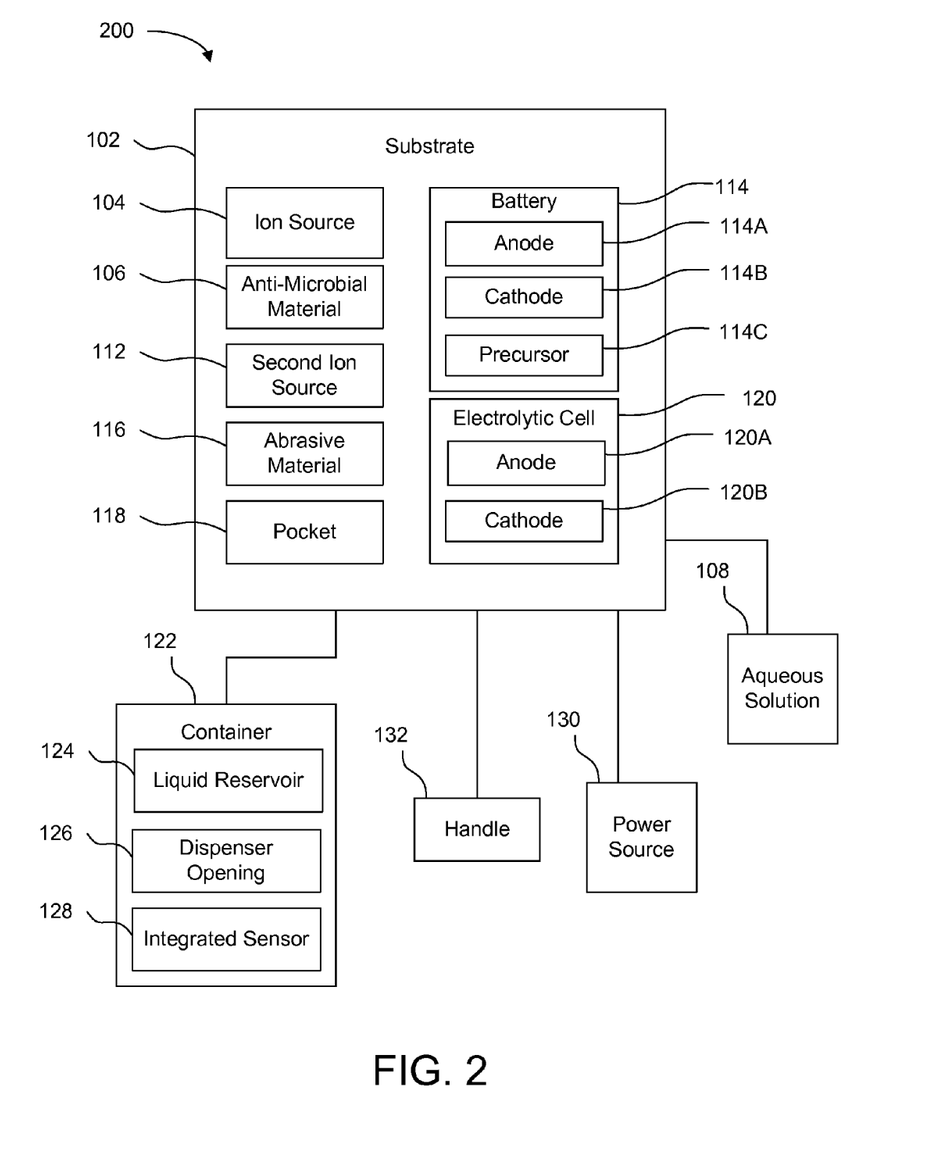
FIG. 2 depicts a schematic diagram of one embodiment of an apparatus for anti-microbial disinfecting.

FIG. 2 depicts a schematic diagram of another embodiment of an anti-microbial disinfecting wipe 200. Although the illustrated wipe 200 is shown and described with certain components and functionality and in conjunction with certain components, other embodiments of the wipe 200 may include fewer or more components to implement less or more functionality. The illustrated embodiment 200 includes similar components and functionality as the illustrated embodiment 100.

While FIG. 2 depicts various components and functionality as described more fully below, not all embodiments include all of the components depicted. Some embodiments include only some of the components described to implement the described functionality. By way of example, various components described below may convert an ion source or anti-microbial material into an anti-microbial solution and each component may be separately utilized in separate embodiments.

The illustrated embodiments depicts an anti-microbial disinfecting wipe 200, including an anti-microbial material 106, an ion source 104, a second ion source 112, a battery 114, an abrasive material 116, a pocket 118, and an electrolytic cell 120. The illustrated embodiment also depicts a container 122 including a liquid reservoir 124, a dispenser opening 126, and an integrated sensor 128. The illustrated embodiment also depicts the aqueous solution 108, a power source 130, and a handle 132.

Some embodiments include a battery or galvanic cell 114. In some embodiments, the battery 114 includes a battery anode 114A and a battery cathode 114B. In some embodiments, the battery anode 114A includes zinc, magnesium, aluminum, and/or other suitable material. In some embodiments, the battery cathode 114B includes carbon, silver chloride, silver oxide, manganese oxide, and/or other suitable material. In some embodiments, the aqueous solution 108 is used to activate the battery 114. In some embodiments, the aqueous solution 108 includes a sodium chloride solution. In some embodiments, the aqueous solution 108 used to activate the battery 114 includes a buffered sodium chloride solution. In some embodiments, a solid sodium chloride is embedded into the substrate 102 and produces a sodium chloride solution when the wipe 100 is moistened by an aqueous solution 108. In some embodiments, the substrate 102 acts as an insulating layer between the battery anode 114A and battery cathode 114B. In some embodiments, the battery anode 114A and/or the battery cathode 114B is printed entirely or in part onto the substrate 102. In some embodiments, the battery anode 114A and/or the battery cathode 114B is embedded entirely or in part into the substrate 102. In some embodiments a plurality of batteries 114 are used. In some embodiments a plurality of batteries 114 are configured with electrical communication, in series and/or in parallel, to increase voltage and/or current. In some embodiments, the battery 114 is configured to generate at least 3 volts. In some embodiments, the battery 114 is configured to generate at least 6 volts.

In some embodiments, a precursor material 114C may be attached to one of the anode 114A, the cathode 114B, and the substrate 102. In some embodiments, the precursor material 114C is a salt or other ion source such that when the cathode 114B and the anode 114A are in contact with a liquid or aqueous solution 108, a galvanic cell 114 is formed where ions form an anti-microbial solution 110. The salt may be sodium chloride and the galvanic cell 114 may change the sodium chloride into sodium hypochlorite in the presence of the aqueous solution 108. In some embodiment, the precursor material 114C is one of AgO, AgCl, AgBr, and $Ag_2O$ which participates in a reaction under the influence of the galvanic cell to form an antimicrobial solution 110 containing silver or silver ions. The anode 114A and the cathode 114B may include or be formed out of a precursor material 114C that either oxidized or reduces in a galvanic cell configuration to form the antimicrobial solution 110. The precursor material 114C in the substrate 102, anode 114A, or cathode 114B may include Al, Mg, Zn, C, Ag, Ca, Na, halides containing these materials, or some other suitable precursor material to facilitate the formation of an antimicrobial solution 110 under the influence of the galvanic cell 114, or as will be discussed below, under the influence of a power source 130 such as a battery. In one embodiment, the aqueous solution 108 is citric acid and the precursor material 114C contains Ag, such that silver citrate is formed.

In some embodiments, an additional ion source or second ion source 112 is embedded into the substrate 102. In some embodiments, exposure of the second ion source 112 to a solution dissociates second ion source 112, resulting in an aqueous solution 108, which may be used to activate the battery 114. In some embodiments, the additional ion source 112 does not contain anions that will react with any anti-microbial ions to form a precipitate.

In some embodiments, at least one of the anode 114A and the cathode 114B are printed onto the substrate 102. The anode 114A and the cathode 114B may be printed on opposing ends or the same end of a first side of the substrate 102. In some embodiments, the substrate 102 may have multiply plies and the anode 114A may be attached to a first ply and the cathode 114B may be attached to a second ply.

Some embodiments include an electrolytic cell configuration 120. In some embodiments, the ion source 104 may be an electrolytic cell 120. In some embodiments, the electrolytic cell includes an electrolytic anode 120A and a cathode 120B in electrical communication to produce anti-microbial ions when current is applied across the electrolytic cell 120. In some embodiments, the anode 120A includes an oxidizable metal.

In some embodiments, an electrolytic cell 120 includes a silver electrolytic anode 120A and an electrolytic cathode 120B to produce silver ions when a current is applied across the electrolytic anode 120A and the electrolytic cathode 120B. In some embodiments, the electrolytic anode 120A includes pure elemental silver, 99.99% silver, greater than 95% silver, greater than 90% silver, and/or metal coated with silver. In some embodiments, the electrolytic cathode 120B includes pure elemental silver, 99.99% silver, greater than 95% silver, greater than 90% silver, metal coated with silver and/or a less reactive metal than silver.

The skilled artisan will understand that the rate and quantity of silver ions produced by the electrolytic cell 120 may be controlled by controlling the voltage and/or current applied to the electrolytic anode 120A and the electrolytic cathode 120B. The rate and quantity of silver ions produced may also be controlled by the duration that the current is applied to the electrolytic anode 120A and the electrolytic cathode 120B. The rate and quantity of silver ions produced may also be controlled by the size and shape of the electrolytic anode 120A and the electrolytic cathode 120B.

In some embodiments, the electrolytic anode 120A and the electrolytic cathode 120B are configured such that an optimal concentration of silver ions is approximated in the anti-microbial solution 110. In some embodiments, the optimal concentration of silver ions is about 0.03 g/L. In some embodiments, the optimal concentration of silver ions is between about 0.02 and 0.04 g/L.

In some embodiments, the electrolytic cell 120 includes an electrolytic anode 120A including carbon, an electrolytic cathode 120B including carbon, and a sodium chloride solution to produce a sodium hypochlorite anti-microbial solution 110. In some embodiments, the carbon electrolytic anode 120A and the carbon electrolytic cathode 120B are configured to be printed onto the substrate 102 as an ink. In some embodiments, the carbon electrolytic anode 120A and the carbon electrolytic cathode 120B are configured to be embedded into the substrate 102. In some embodiments, the electrolytic cell 120 is configured to produce a sufficient concentration of sodium hypochlorite to achieve an effective anti-microbial disinfecting solution 110. The aqueous solution 108 used in the electrolytic cell 120 may be same or different than the aqueous solution 108 used to activate the battery 114. In some embodiments, the aqueous solution 108 used in the electrolytic cell 120 does not contain anions that will react with silver ions and form a precipitate.

In some embodiments, the electrolytic cell 120 comprises an electrolytic anode 120A and an electrolytic cathode 120B powered by sufficient voltage and/or current to produce an anti-microbial ozonated water solution. In some embodiments, the electrolytic cell 120 is configured to produce sufficient ozonated water to achieve an effective anti-microbial disinfecting solution 110. In some embodiments, the electrolytic anode 120A and the electrolytic cathode 120B are configured to be printed onto the substrate 102 as an ink. In some embodiments, the electrolytic anode 120A and the electrolytic cathode 120B are screen printed onto the substrate 102 to make the anti-microbial disinfectant wipe. In some embodiments, the electrolytic anode 120A and the electrolytic cathode 120B are configured to be embedded into the substrate 102. In some embodiments, the electrolytic anode 120A and electrolytic cathode 120B are integrated into the flexible substrate 102 between different plies of the substrate 102. In some embodiments, the electrolytic anode 120A and electrolytic cathode 120B are integrated in the substrate on opposite ends of the same side of the flexible substrate 102. In some embodiments, a series of electrolytic anodes 120A and electrolytic cathodes 120B in electrical communication may be integrated in the substrate 102. In some embodiments, the battery 114 may be attached to the electrolytic anodes 120A and electrolytic cathodes 120B with further electrical communication. In some embodiments, the electrolytic anode 120A and the electrolytic cathode 120B are configured to receive at least 3 volts. In some embodiments, the electrolytic anode 120A and the electrolytic cathode 120B are configured to receive at least 6 volts. In some embodiments, the electrolytic anode 120A includes $Bi_2RuO_5$, platinum, silver, gold, or mixtures thereof. In some embodiments, the electrolytic cathode 120B includes nickel, silver, carbon, platinum, or mixtures thereof. In some embodiments, the anode 120A or the cathode 120B may include at least one of carbon, silver, gold, platinum, titanium, precious metal, and rare earth metal.

In some embodiments, the oxidizable compound is configured such that, when the anode 120A and cathode 120B are in contact with a sodium chloride solution, the electrolytic cell 120 produces a sodium hypochlorite anti-microbial solution 110. In other embodiments, the electrolytic cell 120 is further configured to produce an anti-microbial ozonated water solution 110 upon activation of the electrolytic cell 120. In some embodiments, an additional ion source 112 is embedded into the substrate 102, such that upon exposure to a solution the additional ion source 112 dissociates resulting in an aqueous solution 108, which may be used in the electrolytic cell 120 or to activate the battery 114. In some embodiment, the additional ion source 112 does not contain anions that will react with any anti-microbial ions to form a precipitate.

It will be appreciated by those of skill in the art that a combination of electrode materials, coatings and precursor materials may be configured in a variety of ways to produce an anti-microbial solution 110 when voltage is applied to an anode and a cathode. For example, the electrolytic cell configuration 120 may facilitate the reaction of sodium chloride to produce sodium hypochlorite. In another embodiment the electrolytic cell may facilitate a reaction containing $H_2O$ to produce an anti-microbial solution containing ozonated water solution upon activation of the electrolytic cell.

In some embodiments, the anode and/or cathode may include C, Ag, Au, Pt, Ti, a precious metal, or a rare earth metal. The precursor material may include a halide containing compound such as $Ca(Cl_2)$, $NaCl$, $Na(Cl_2)$, and $Mg(Cl_2)$, where Chlorine may be substituted for other suitable halides such as Iodine, Bromine, or Fluorine. In this configuration, under the influence of a power source 130 to the electrolytic cell configuration 120, one or more of the following corresponding reactions may occur to form an anti-microbial solution:

$Ca(Cl_2) \rightarrow Ca(ClO)_2$ $NaCl \rightarrow NaClO$ $Na(Cl_2) \rightarrow Na(ClO)_2$ $Mg(Cl_2) \rightarrow Mg(ClO)_2$ In some embodiments, the substrate 102 further includes an abrasive material 116. In some embodiments, the abrasive material is an inert-based abrasive material. The abrasive material 116 may include ceramic, glass, minerals, synthetic stones, natural fibers, polishing agents, metal pellets, silica, or combinations thereof. The abrasive material 116 may be coated onto, adhesively bonded to, or otherwise integrated into the substrate 102. The inert-based abrasive material 116 allows for more effective cleansing and scrubbing with the anti-microbial disinfectant wipe.

In some embodiments, the substrate 102 may be configured to further include a pocket 118 to hold the anti-microbial ion source 104, or anti-microbial material 106. In some embodiments, the substrate 102 may be configured to include a refillable pocket 118 to hold anti-microbial ion source 104, which may be refilled with subsequent anti-microbial ion sources 104. In some embodiments, the substrate 102 may include one ply. In some embodiments, the flexible substrate 102 may be more than one ply. In some embodiments, the pocket 118 may be formed on the substrate 102 by sewing suitable material onto the substrate 102. In some embodiments, the pocket 118 may be formed in the substrate 102 between a first ply and a second ply of the substrate 102. The pocket 118 may hold the anti-microbial ion source 104 in electrochemical cell form or other suitable forms where the anti-microbial ion source 104 may dissolve in the presence of water to form anti-microbial solution 110 beneficial for cleaning. In some embodiments, the pocket 118 may be further configured to contain the battery 114. In some embodiments, the battery 114 in the pocket 118 may be connected to an electrolytic cell 120 internal to the pocket 118 or external to the pocket 118 via electrical communication. It will be appreciated by those of skill in the art that the pocket 118 may be in any number of configurations to retain an anti-microbial ion source 104 and allow the replacement of anti-microbial ion source 104 into the pocket 118.

In some embodiments, the wipe 200 includes a power source 130 in electrical communication with the anode 120A and the cathode 120B. In some embodiments, the anode 120A, the cathode 120B, and the power source 130 are configured to form an electrolytic cell 120, such that the ion source 104 or the precursor material participates in a reaction to form an antimicrobial solution 110 when voltage is applied from the power source 130 to the anode 120A and the cathode 120B. Similar to the galvanic cell 114, the electrolytic cell 120 may have an anode 120A that at least partially includes a precursor material that is an oxidizable compound capable of oxidizing to an anti-microbial ion species. In some embodiments, the oxidizable compound includes an oxidizable silver, wherein the anti-microbial ion species includes silver ions.

In one embodiment, the power source 130 polarizes the anode 120A and/or cathode 120B, such that portions of the wipe 200 become "charged." These charged portions of the wipe 200 attract dirt and/or microbes that are oppositely charged and remove them from surfaces or whatever is being cleaned. In some embodiments, the battery 114 is the power source 130.

Some embodiments include a container 122. In some embodiments, the anti-microbial wipe 100 is configured to be dispensed as single wipes from a container 122. In some embodiments, the container 122 is configured to hold a plurality of dry wipes. In some embodiments, a single wipe at a time is dispensed from the container 122 through a dispensing opening 126. The single wipe is then used and discarded.

In some embodiments, the wipe is configured as a single-use wipe 100, sealed individually in an enclosed container 122. In some embodiments, the substrate 102 and the anti-microbial ion source 104 are enclosed in the enclosed container 122 without any liquid or aqueous solution 108. In some embodiments, a liquid reservoir 124 of appropriate aqueous solution 108 is integrated into the enclosed container 122. In some embodiments, a user releases the aqueous solution 108 from the liquid reservoir 124 to fill the enclosed container 122 to activate the anti-microbial ion source 104. In some embodiments, the liquid reservoir 124 is prepackaged with the appropriate solution. In some embodiments, the user fills the liquid reservoir 124 with the appropriate solution.

In some embodiments, the enclosed container 122 is further configured with an integrated sensor 128. In some embodiments, the integrated sensor 128 includes a specific gravity sensor, a hydrometer, a pH sensor, a temperature sensor, and/or an ionic strength sensor. In some embodiments, the integrated sensor 128 is configured to relay the anti-microbial ion concentration of the enclosed container 122 to the user. In some embodiments, the integrated sensor 128 is configured to indicate to the user when the anti-microbial ion concentration of the anti-microbial ion solution 110 has reached an optimal level. In some embodiments, the integrated sensor 128 is configured to indicate to the user when the anti-microbial ion concentration of the anti-microbial ion solution 110 has surpassed an optimal level. In some embodiments, the integrated sensor 128 is configured to indicate to the user when the wipe and anti-microbial ion solution 110 is ready for use. In some embodiments, the integrated sensor 128 is configured to indicate to the user when the anti-microbial ion solution 110 is not ready for use.

In some embodiments, the battery 114 or power source 130 is disposed in a handle 132. The handle 132 may be configured to include corresponding electrical communication between a battery 114 and an electrolytic anode 120A and an electrolytic cathode 120B. In some embodiments, the handle 132 may be configured to removably attach to the electrolytic anode 120A and an electrolytic cathode 120B such that a handle 132 may be utilized with more than one electrochemically-activated anti-microbial disinfectant wipe.

In some embodiments, the power source 130 is integrated into the handle 132. The handle 132 may be a brush or mop handle or any apparatus suitable for gripping and wiping. The handle 132 may be configured for electrical communication with the anode 120A and cathode 120B. The handle 132 may be removably attached to the substrate 102. In one embodiment both the anode 120A and cathode 120B are attached to the substrate 102.

Figure 3:
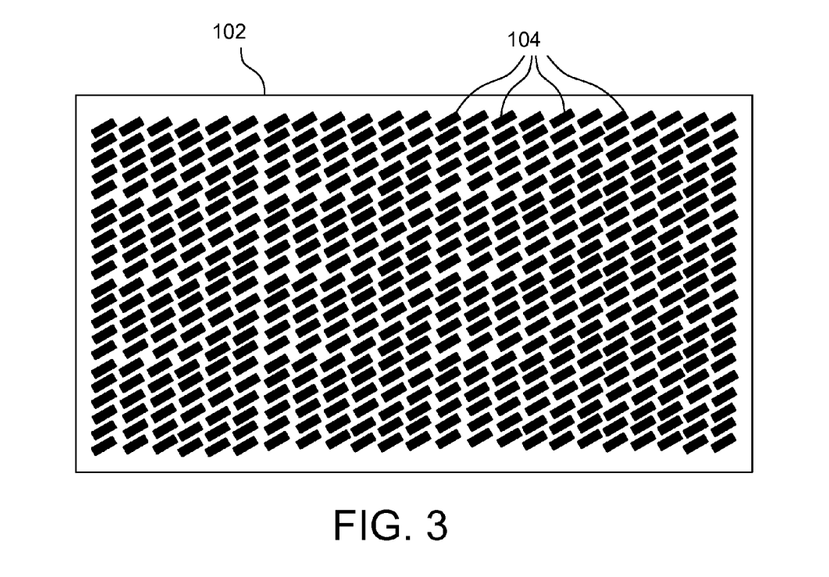
FIG. 3 depicts one embodiment of the substrate and anti-microbial material of an apparatus for anti-bacterial disinfecting.

FIG. 3 depicts one embodiment of the substrate 102 and ion source 104 of FIGS. 1 and 2, with the ion source 104 printed on the substrate 102. The illustrated embodiment includes an anti-microbial ion source 104 embedded into the substrate 102. The anti-microbial ion source 104 is configured to dissolve upon exposure to an aqueous solution 108 and create an anti-microbial solution 110.

Figure 4A:
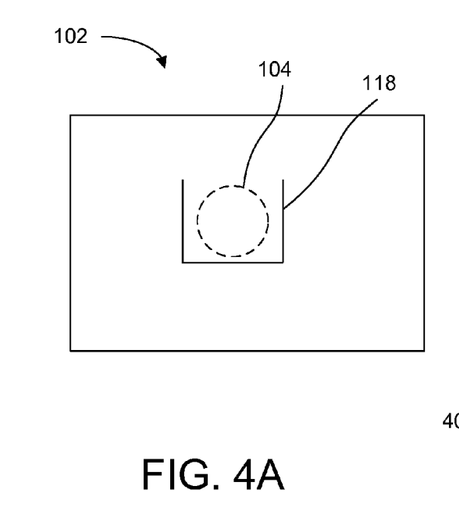
FIG. 4A depicts one embodiment of the substrate including a pocket and anti-microbial material of an apparatus for anti-bacterial disinfecting.

FIG. 4A depicts one embodiment of the substrate 102 including a pocket 118 and an anti-microbial ion source 104. In some embodiments, the substrate 102 may be configured to further include a pocket 118 to hold the anti-microbial ion source 104. In some embodiments, the substrate 102 may be configured to comprise a refillable pocket 118 to hold the anti-microbial ion source 104, which may be refilled with subsequent anti-microbial ion sources 104. In some embodiments, the pocket 118 may be formed on the substrate 102 by sewing suitable material onto the substrate 102. The pocket 118 may hold the anti-microbial ion source 104 in electrochemical cell form or other suitable forms where the anti-microbial ion source 104 may dissolve in the presence of water or an aqueous solution 108 to form anti-microbial solution 110 beneficial for cleaning.

Figure 4B:
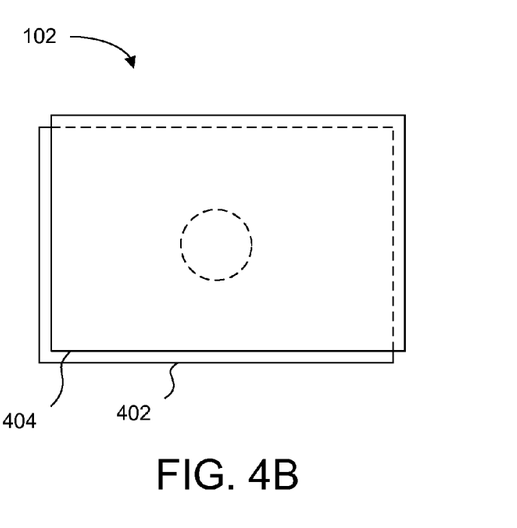
FIG. 4B depicts one embodiment of the substrate and anti-microbial material in between two plies.

FIG. 4B depicts one embodiment of the substrate 102 and an anti-microbial ion source 104 in between two plies. In some embodiments, the substrate 102 may include one ply 402. In other embodiments, the substrate 102 may be more than one ply. In some embodiments, the pocket 118 may be formed in the substrate 102 between two plies (402, 404) of the substrate 102.

Figure 5A:
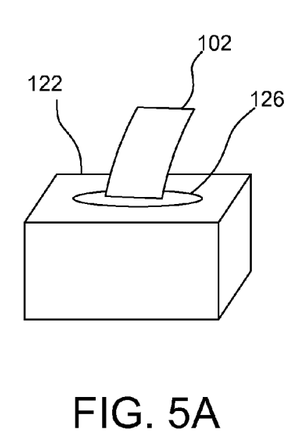
FIG. 5A depicts one embodiment of the container of FIG. 2.

FIG. 5A depicts one embodiment of the container 122 of FIG. 2. In some embodiments, the anti-microbial wipe 100 is configured to be dispensed as single wipes from a container 122. In some embodiments, the container 122 is configured to hold a plurality of dry wipes. In some embodiments, a single wipe at a time is dispensed from the container 122 through a dispenser opening 126. The single wipe is then used and discarded. In some embodiments, the dispenser opening is configured to apply the aqueous solution 108 as the wipe is removed from the container 122.

Figure 5B:
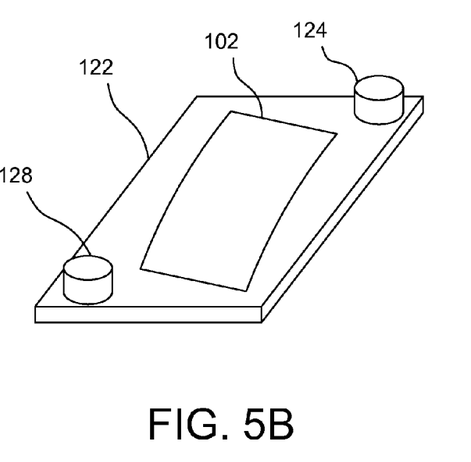
FIG. 5B depicts one embodiment of the container of FIG. 2.

FIG. 5B depicts one embodiment of the container 122 of FIG. 2. In some embodiments, a wipe is configured as a single-use wipe, sealed individually in an enclosed container 122. In some embodiments, the substrate 102 and the anti-microbial ion source 104 are enclosed in the enclosed container 122 without any liquid or aqueous solution 108. In some embodiments, a liquid reservoir 124 of appropriate solution is integrated into the enclosed container 122. In some embodiments, a user releases the liquid or an aqueous solution 108 from the liquid reservoir 124 to fill the enclosed container 122 to activate the anti-microbial ion source 104. In some embodiments, the liquid reservoir 124 is prepackaged with the appropriate solution. In some embodiments, the user fills the liquid reservoir 124 with the appropriate solution.

In some embodiments, the enclosed container 122 is further configured with an integrated sensor 128. In some embodiments, the integrated sensor 128 includes the components and functionality described above in conjunction with FIG. 2.

Figure 6:
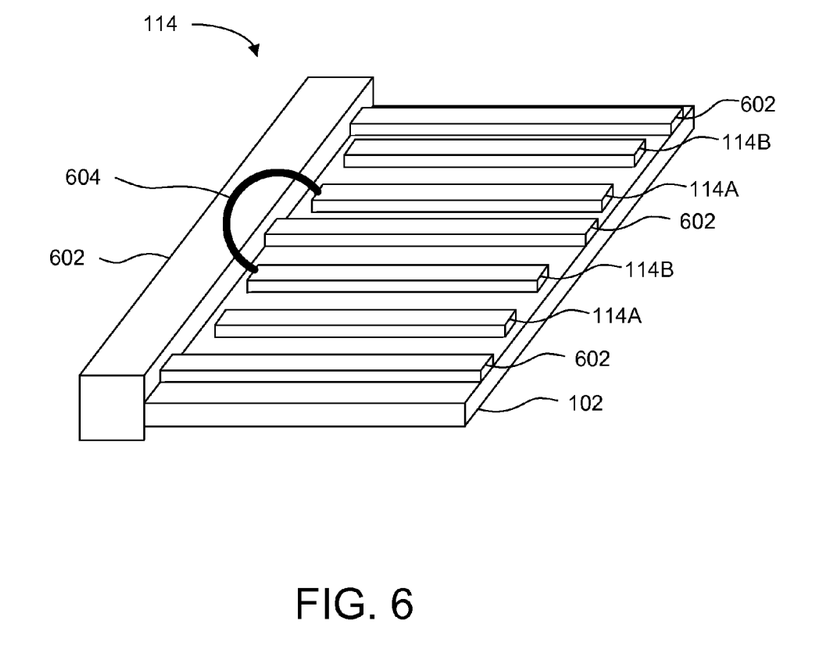
FIG. 6 depicts one embodiment of the battery of FIG. 2.

FIG. 6 depicts one embodiment of the battery 114 of FIG. 2. The illustrated embodiment includes an insulating layer 602 isolating and/or insulating a battery anode 114A and a battery cathode 114B to create a battery cell. In some embodiments, several battery cells are connected with electrical communication 604 in parallel or in series. In some embodiments, when the battery 114 is moistened with an aqueous solution 108, an electric current is produced.

Figure 7:
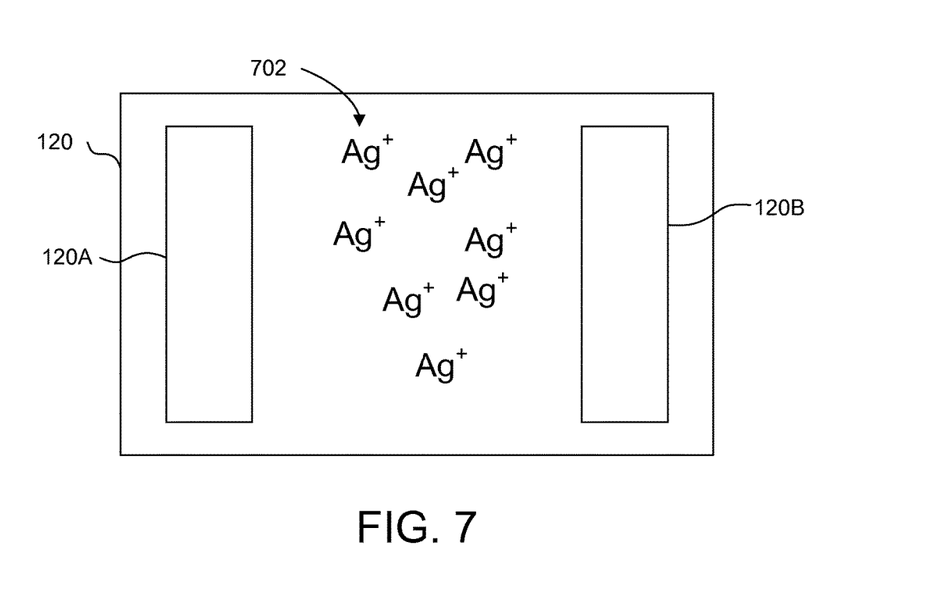
FIG. 7 depicts one embodiment of the electrolytic cell of FIG. 3.

FIG. 7 depicts one embodiment of the electrolytic cell of FIG. 3. In the illustrated embodiment, the electrolytic cell 120 includes an electrolytic anode 120A, an electrolytic cathode 120B, and water and/or an aqueous solution 108. The electrolytic anode 120A includes oxidizable silver capable of undergoing oxidation under the influence of an electric current as follows:

to produce silver ions 702.

Figure 8:
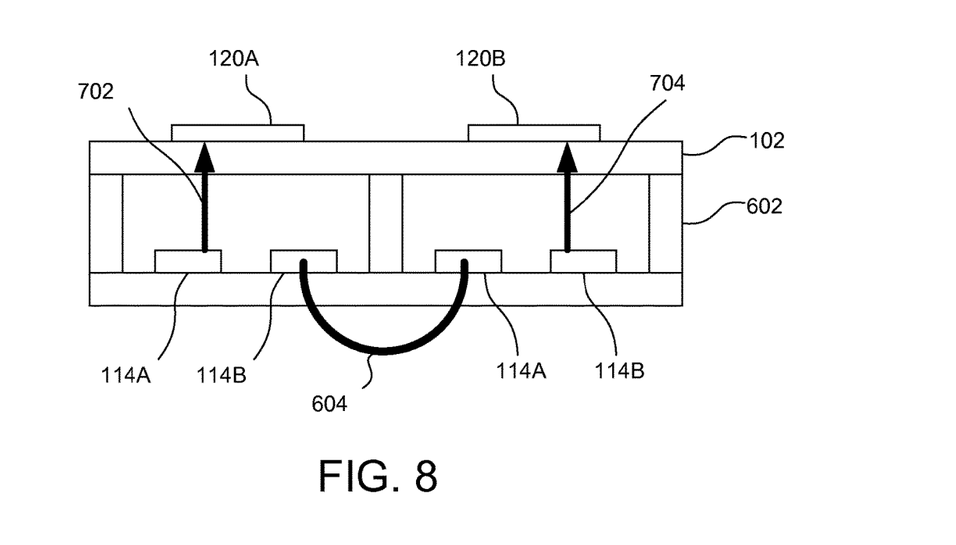
FIG. 8 depicts one embodiment of a battery and electrolytic cell in connection with a substrate

FIG. 8 depicts one embodiment of a battery 114 and electrolytic cell 120 in connection with a substrate 102. The illustrated embodiment includes a battery 114 and an electrolytic cell 120 which are combined to produce an anti-microbial solution 110. In some embodiments, a battery 114 is configured as described above and isolated and/or insulated from an electrolytic cell 120 that is configured as described above. In some embodiments, the battery 114 is embedded in the substrate 102 to isolate the battery 114 from the electrolytic cell 120. In some embodiments, the battery produces current when water and/or an aqueous solution 108 are applied to the battery anode 114A and the battery cathode 114B. Current from the battery 114 is then applied 702, 704 to the electrolytic cell 120. When current is applied to the electrolytic cell 120, current is applied to the electrolytic anode 120A and the electrolytic cathode 120B to produce anti-microbial solution 110, as is described above.

As an example, the battery 114 includes a battery anode 114A including zinc and a battery cathode 114B including manganese oxide. Both the battery anode 114A and the battery cathode 114B are printed onto an inner layer of the substrate 102 that is insulated and isolated from an outer layer of the substrate 102. Solid sodium chloride is embedded into the inner layer of the substrate 102. The inner layer of the substrate 102 is moistened with 2 ml of distilled water to dissolve the solid sodium chloride and produce a sodium chloride solution. The sodium chloride solution activates the battery 114. The battery 114 powers the electrolytic cell 120.

The electrolytic cell 120 includes an electrolytic anode 120A including 99.99% silver and an electrolytic cathode 120B including 99.99% silver, both of which are printed onto the outer layer of the substrate 102. The silver electrolytic anode 120A includes sufficient silver metal to create a total of about 2 ml of silver ion anti-microbial solution at a concentration of about 0.03 g/L silver ion concentration. Solid citric acid is embedded into the substrate 102 to produce an aqueous solution 108 of citric acid when the outer layer of the substrate 102 is moistened. The outer layer of the substrate 102 is moistened with 2 ml of distilled water. The electrolytic cell 120 is powered and produces a silver ion anti-microbial solution 110 that is absorbed into the substrate 102. When sufficient time passes to reach an optimal concentration of about 0.03 g/L, the wipe is used to disinfect surfaces.

Figure 9A:
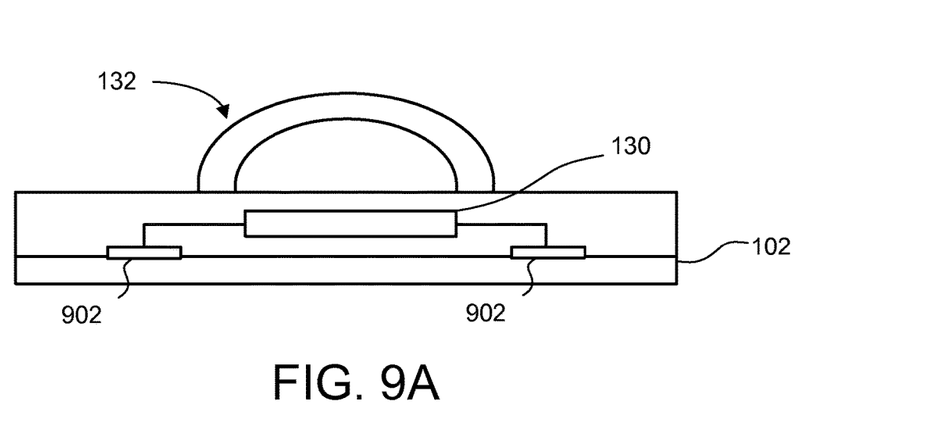
FIG. 9A depicts one embodiment of the handle of FIG. 2.

FIG. 9A depicts one embodiment of the handle 132 of FIG. 2. In some embodiments, the handle may be a brush or mop handle or any apparatus suitable for gripping and wiping. The handle may be configured for electrical communication with an anode 120A and a cathode 120B. In some embodiments, a power source 130 is integrated into the handle 132. The handle 132 may be removably attached to the substrate 102. In one embodiment both the anode 120A and cathode 120B (not shown) are attached to the substrate 102. Where the handle 132 is attached to the substrate 102, the handle 132 may have contact points or pads 902 that are connected to the power source 130 and that correspond to similarly placed contact points or pads configured in the substrate 102. The contact points or pads of the substrate may be the anode 120A and the cathode 120B.

Figure 9B:
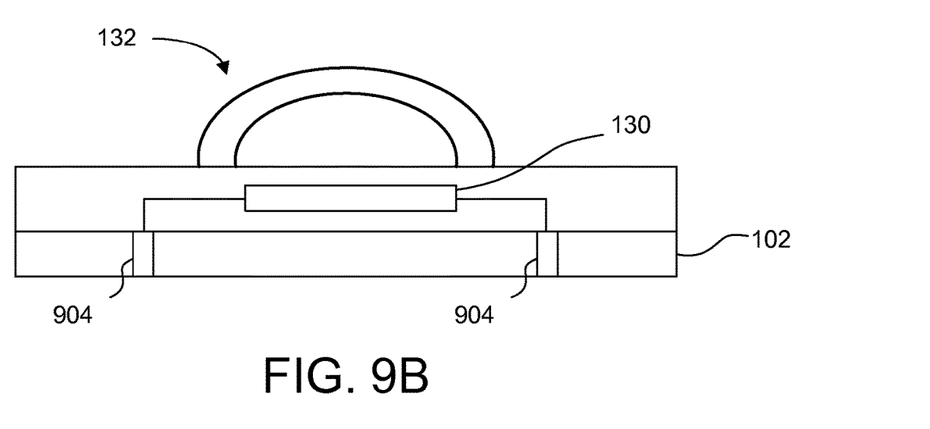
FIG. 9B depicts another embodiment of the handle of FIG. 2.

FIG. 9B depicts another embodiment of the handle 132 of FIG. 2. In some embodiments, the handle 132 may include posts 904 that are in electrical communication with the power source 130 such that when the substrate 102 is attached to the handle 132, one of the posts 904 is in electrical communication with an anode and another of the posts 904 is in electrical communication with the cathode on the substrate 102. It will be appreciated by those of skill in the art that a combination of posts and pads may be utilized such that whatever side of the substrate 102 or wherever the anode and cathode are positioned on the substrate 102, the power source will be in electrical communication with the anode and the cathode when the substrate 102 is attached to the handle 132.

Figure 9C:
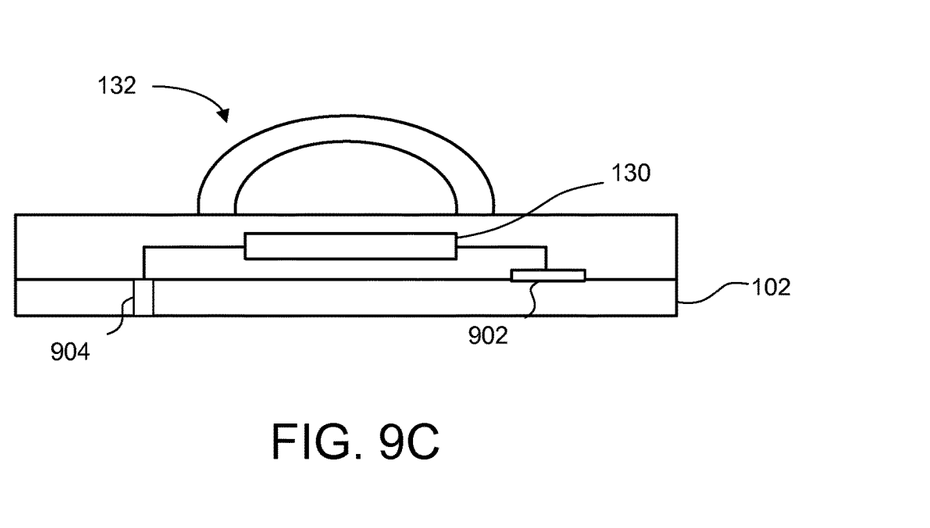
FIG. 9C depicts another embodiment of the handle of FIG. 2.

FIG. 9C depicts another embodiment of the handle 132 of FIG. 2. In some embodiments, only one of the anode 120A or cathode 120B is attached to the substrate 102, while the other is attached to the handle 132. In some embodiments, the anode 120A or cathode 120B may be screen printed along a portion of, or the entire side or, the substrate 102. The side may be the side opposite from the handle 132. The substrate 102 in such embodiments may be electronically insulated such that the anode 120A and cathode 120B are insulated from each other.

Methods for using the foregoing anti-microbial disinfecting wipes outlined in FIGS. 1-9C include moistening a flexible substrate with an aqueous solution, dissolving an anti-microbial material in contact with the flexible substrate with the aqueous solution to create an anti-microbial solution, and disinfecting a surface of an object with the anti-microbial solution containing flexible substrate. Other embodiments include activating an electrolytic cell on the flexible substrate by completing a circuit with an aqueous solution, and producing an anti-microbial solution with the electrolytic cell. Other embodiments include activating a battery on the flexible substrate with an aqueous solution, energizing an electrolytic cell to produce an anti-microbial solution, and disinfecting surfaces with the substrate. Persons skilled in the art will recognize other methods consistent with the embodiments described herein.

The present invention may be embodied in other specific forms without departing from its basic principles or essential characteristics. The described embodiments are to be considered in all respects illustrative and not restrictive. The scope of the invention is therefore indicated by the appended claims rather than by the foregoing description. All changes which come within the meaning and range of the equivalency of the claims are to be embraced within their scope.

Each aspect of the aforementioned embodiments may or may not be present in any or all of the embodiments and reference to one aspect or characteristic in an embodiment should not be interpreted to mean that it is not or cannot be present in another embodiment. The present invention may be embodied in other specific forms without departing from its basic principles or essential characteristics. The described embodiments are to be considered in all respects illustrative and not restrictive. The scope of the invention is therefore indicated by the appended claims rather than by the foregoing description. All changes which come within the meaning and range of the equivalency of the claims are to be embraced within their scope In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. The combination of a wipe for anti-microbial disinfecting and a wipe holder, the wipe comprising:
   a flexible substrate, wherein the flexible substrate is made entirely or in part of woven fiber cloth, non-woven fiber cloth, woven synthetic cloth, non-woven synthetic cloth, or natural fiber cloth; an anode and a cathode, wherein the anode and the cathode are attached to the flexible substrate, wherein at least one of the anode, the cathode, and flexible substrate comprises a first anti-microbial ion source; wherein the wipe is configured to form a galvanic cell when an aqueous solution contacts the anode and the cathode; and wherein the galvanic cell is configured to cause the first anti-microbial ion source to create a first anti-microbial solution;
   a second anti-microbial source integrated on the substrate, wherein the second anti-microbial source is configured to dissolve in the aqueous solution to form a second anti-microbial solution, wherein the flexible substrate is configured to absorb the second anti-microbial solution for use in cleaning, the second anti-microbial source comprising an anti-microbial material carried by the flexible substrate, the flexible substrate comprising a pocket configured to contain the anti-microbial material; and
   the wipe holder comprising a protruding handle structured for grasping by a human hand and retention structure associated with the handle being configured and arranged to hold the wipe in removable registration with respect to the handle to permit a user to manipulate the handle to consequently move the wipe across a surface to spread a portion of the first anti-microbial solution there-on to disinfect the surface.

2. The combination of claim 1, wherein the anode comprises at least one of Zn, Mg, and Al, wherein at least one of the anode and the cathode are printed onto the flexible substrate.

3. The combination of claim 1, wherein the cathode comprises at least one of AgO, AgCl, AgBr, and $Ag_2O$, wherein at least one of the anode and the cathode are printed onto the flexible substrate.

4. The combination of claim 1, wherein the ion source is sodium chloride, wherein the galvanic cell changes the sodium chloride into sodium hypochlorite in the presence of the aqueous solution.

5. The combination of claim 1, wherein the anode and the cathode are printed on opposing ends of a first side of the flexible substrate.

6. The combination according to claim 1, wherein:
   the anti-microbial material comprises at least one of the following: sodium dichloroisocyanurate, potassium peroxymonosulfate, calcium hypochlorite, benzalkonium chloride, dodecyl dimethyl benzyl ammonium chloride, lauryl dimethyl benzyl ammonium chloride, quaternary ammonium salt, and sodium per carbonate.

7. The combination according to claim 1, wherein:
   the anti-microbial material comprises a silver ion source, wherein the silver ion source further comprises at least one of the following: silver dihydrogen citrate, silver nitrate, silver fluoride, silver acetate, silver permanganate, silver sulfate, silver nitrite, silver bromate, silver salicylate, silver iodate, silver dichromate, silver chromate, silver carbonate, silver citrate, silver phosphate, and silver chloride.

8. The combination according to claim 7, wherein:
dissolution of the silver ion source in the aqueous solution results in a silver ion anti-microbial solution.

9. The combination according to claim 1, wherein:
the flexible substrate comprises a first ply and a second ply, wherein the pocket is formed between the first ply and the second ply of the flexible substrate.

10. The combination according to claim 1, wherein:
the wipe further comprises an abrasive material embedded in the flexible substrate, wherein the abrasive material is comprised of at least one of ceramic, glass, minerals, synthetic stones, natural fibers, polishing agents, metal pellets, and silica.

11. A wipe for anti-microbial disinfecting, the wipe comprising:
a flexible substrate, wherein the flexible substrate is made entirely or in part of woven fiber cloth, non-woven fiber cloth, woven synthetic cloth, non-woven synthetic cloth, or natural fiber cloth;
an anode and a cathode, wherein the anode and the cathode are attached to the flexible substrate, wherein at least one of the anode, the cathode, and flexible substrate comprises a first anti-microbial ion source; wherein the wipe is configured to form a galvanic cell when an aqueous solution contacts the anode and the cathode; and wherein the galvanic cell is configured to cause the first anti-microbial ion source to create a first anti-microbial solution; and
a second anti-microbial source is integrated on the substrate, wherein the second anti-microbial source is configured to dissolve in an aqueous solution to form a second anti-microbial solution, wherein the flexible substrate is configured to absorb the second anti-microbial solution for use in cleaning, wherein:
the second anti-microbial source comprises an anti-microbial material, wherein the anti-microbial material is carried by the flexible substrate; and
the flexible substrate comprises a pocket, wherein the pocket is configured to contain the anti-microbial material.

12. The wipe according to claim 11, wherein:
the anti-microbial material comprises at least one of the following: sodium dichloroisocyanurate, potassium peroxymonosulfate, calcium hypochlorite, benzalkonium chloride, dodecyl dimethyl benzyl ammonium chloride, lauryl dimethyl benzyl ammonium chloride, quaternary ammonium salt, and sodium per carbonate.

13. The wipe according to claim 11, wherein:
the anti-microbial material comprises a silver ion source, wherein the silver ion source further comprises at least one of the following: silver dihydrogen citrate, silver nitrate, silver fluoride, silver acetate, silver permanganate, silver sulfate, silver nitrite, silver bromate, silver salicylate, silver iodate, silver dichromate, silver chromate, silver carbonate, silver citrate, silver phosphate, and silver chloride; and
dissolution of the silver ion source in the aqueous solution results in a silver ion anti-microbial solution.

14. The wipe according to claim 11, wherein:
the flexible substrate comprises a first ply and a second ply, wherein the pocket is formed between the first ply and the second ply of the flexible substrate.

15. The wipe according to claim 11, wherein:
the wipe further comprises an abrasive material embedded in the flexible substrate, wherein the abrasive material is comprised of at least one of ceramic, glass, minerals, synthetic stones, natural fibers, polishing agents, metal pellets, and silica.

* * * * *